US010485637B2

(12) United States Patent
Atkin

(10) Patent No.: US 10,485,637 B2
(45) Date of Patent: Nov. 26, 2019

(54) DENTAL PROSTHETIC ASSEMBLIES AND COUPLING SYSTEMS

(71) Applicant: Dental Milling Solutions, LLC, Saint Louis, MO (US)

(72) Inventor: Scott C. Atkin, Phoenix, AZ (US)

(73) Assignee: Dental Milling Solutions, LLC, Saint Louis, MO (US)

( * ) Notice: Subject to any disclaimer, the term of this patent is extended or adjusted under 35 U.S.C. 154(b) by 0 days.

(21) Appl. No.: 15/785,536

(22) Filed: Oct. 17, 2017

(65) Prior Publication Data

US 2018/0110594 A1 Apr. 26, 2018

Related U.S. Application Data

(60) Provisional application No. 62/412,913, filed on Oct. 26, 2016.

(51) Int. Cl.
*A61C 8/00* (2006.01)
*A61C 13/00* (2006.01)

(52) U.S. Cl.
CPC .......... *A61C 8/0027* (2013.01); *A61C 8/0013* (2013.01); *A61C 8/0016* (2013.01); *A61C 8/0068* (2013.01); *A61C 13/0006* (2013.01)

(58) Field of Classification Search
CPC ... A61C 8/0027; A61C 8/0048; A61C 8/0016; A61C 8/0068; A61C 8/0013; A61C 13/0006; A61C 13/087; A61C 13/01
USPC ........................................................ 433/173
See application file for complete search history.

(56) References Cited

U.S. PATENT DOCUMENTS

| 3,881,251 | A | * | 5/1975 | Valen | A61C 8/0048 433/176 |
| 5,788,492 | A | * | 8/1998 | Weissman | A61C 13/26 433/173 |
| 6,273,721 | B1 | * | 8/2001 | Valen | A61C 8/0022 433/174 |
| 7,785,108 | B2 | | 8/2010 | Tache et al. | |
| 9,668,837 | B2 | | 6/2017 | Jung | |

(Continued)

OTHER PUBLICATIONS

Dental Aegis; "Panthera's Lock 'n' Release Bar Allows Easy Installation, Removal" Mar. 2016, vol. 7, Issue 3, AEGIS Communications, (3 pages).

(Continued)

*Primary Examiner* — Matthew M Nelson
(74) *Attorney, Agent, or Firm* — Christopher R. Carroll; The Small Patent Law Group LLC

(57) ABSTRACT

A dental prosthetic assembly includes a semi-flexible reinforcement bar and a polymer and glass outer layer chemically luted to the semi-reinforcement bar outside of the reinforcement bar. The semi-flexible reinforcement bar forms an interior of the dental prosthetic assembly and at least a portion of the polymer and glass outer layer forms teeth of the dental prosthetic assembly. A coupling system of a dental prosthetic assembly includes pins disposed in openings extending into the dental prosthetic assembly and implant abutments configured to be coupled with a mouth of a patient. The implant anchors have horizontal holes configured to receive the pins. The pins secure the dental prosthetic assembly to the implant abutments by moving into the dental prosthetic assembly through the openings and into the holes of the implant abutments.

10 Claims, 7 Drawing Sheets

(56) References Cited

U.S. PATENT DOCUMENTS

| | | | |
|---|---|---|---|
| 2003/0211444 A1* | 11/2003 | Andrews | A61C 13/0003 433/172 |
| 2012/0171639 A1* | 7/2012 | Berger | A61C 8/0048 433/173 |
| 2015/0147723 A1* | 5/2015 | Berger | A61C 8/0048 433/199.1 |
| 2015/0230891 A1* | 8/2015 | Grobbee | A61C 13/2656 433/199.1 |
| 2016/0270886 A1* | 9/2016 | Schulter | A61C 8/0027 |
| 2019/0046306 A1* | 2/2019 | Berger | A61C 8/0048 |

OTHER PUBLICATIONS

MT Magazine; "Panthera Lock 'n' Release™ Bar", LMT Communications, Inc., 2016 (2 pages).

Panthera Dental; "How It Works", 2016 (5 pages).

* cited by examiner

DENTAL PROSTHETIC ASSEMBLIES AND COUPLING SYSTEMS

CROSS-REFERENCE TO RELATED APPLICATIONS

This application claims priority to U.S. Provisional Application No. 62/412,913, which was filed on 26 Oct. 2016, and the entire disclosure of which is incorporated herein by reference.

FIELD

Embodiments of the subject matter described herein relate to implant supported dental prosthetics.

BACKGROUND

Dental prosthetics, such as fixed dentures, can be used to replace all or some missing teeth in a mouth. Currently known dentures are fabricated from materials that are unable to withstand extended use due to fracturing and disassembly, creating inconvenience and hardship for the patient. For example, some dentures are fabricated from a titanium bar having manufactured teeth bodies (shapes of manufactured teeth are processed on the titanium bar). These materials do not form any chemical bond between the bar, processed acrylic on the bar, and the manufactured teeth. Therefore as a result, the processed acrylic and teeth bodies can separate and break from the titanium bar easily, resulting in a poor choice for a fixed denture.

Other fixed dentures may be milled from solid zirconia. While these types of dentures also suffer from the drawbacks associated with the titanium-acrylic based dentures, the solid zirconia material is a very hard and heavy material and can create significant discomfort for patients while chewing food and general mastication. The solid zirconia dentures have little to no flexibility and therefore can fracture easily.

Currently known dentures may be fixed inside a patients' mouth using screws that extend through the dentures and into facial implants of the patient. The screws tend to be very small and difficult to remove. During servicing of the dentures, attempted removal of these screws can be difficult and risk damage to the screws and the prosthesis. This can result in extensive additional dental work required to remove the damaged or broken screws.

BRIEF DESCRIPTION

In one embodiment, a dental prosthetic assembly includes a semi-flexible reinforcement bar and a polymer/glass outer layer that is chemically luted to the semi-flexible reinforcement bar using a dual cure bonding system. The semi-flexible reinforcement bar forms an interior of the dental prosthetic assembly and the polymer/glass portion of the outer layer forms teeth of the dental prosthetic assembly.

In one embodiment, a coupling system of a dental prosthetic assembly includes pins that move in and out in openings that extend into the dental prosthetic assembly and implant custom abutments that are configured to be coupled with a mouth of a patient. The implant abutments have horizontal holes configured to receive the pins. The pins secure the dental prosthetic assembly to the implant abutments by moving the pins into the dental prosthetic assembly through the openings and into the horizontal holes of the implant abutments.

In one embodiment, a method includes obtaining a semi-flexible reinforcement bar, obtaining a polymer/glass outer layer, chemically bonding the reinforcement bar with the polymer/glass outer layer, and milling artificial teeth into the polymer-based outer layer to form a dental prosthetic assembly. The reinforcement bar forms an interior of the dental prosthetic assembly.

BRIEF DESCRIPTION OF THE DRAWINGS

The subject matter described herein will be better understood from reading the following description of non-limiting embodiments, with reference to the attached drawings, wherein below.

DETAILED DESCRIPTION

Embodiments of the inventive subject matter described herein relate to dental prosthetics, such as dentures, formed from a new combination of materials that remedies many problems associated with currently known dental prosthetics. Other embodiments described herein relate to dental prosthetic coupling systems that allow persons to easily remove the prosthetics inside patients' mouths and re-attach the prosthetics inside the patients' mouths, without significant risk to damaging the patients or prosthetics.

Figure 1:
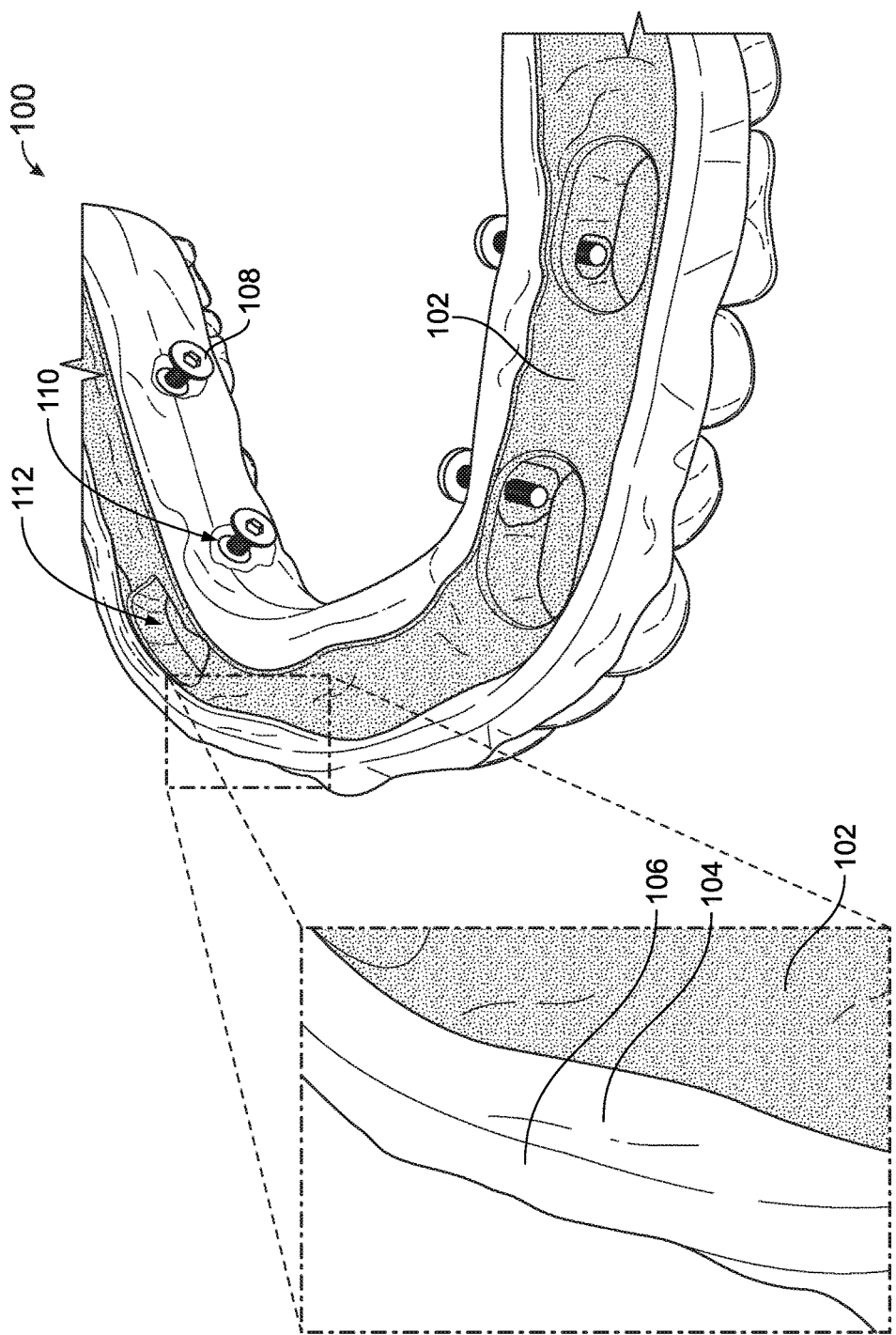
FIG. 1 illustrates a dental prosthetic assembly according to one embodiment of the inventive subject matter described herein.
Figure 2:
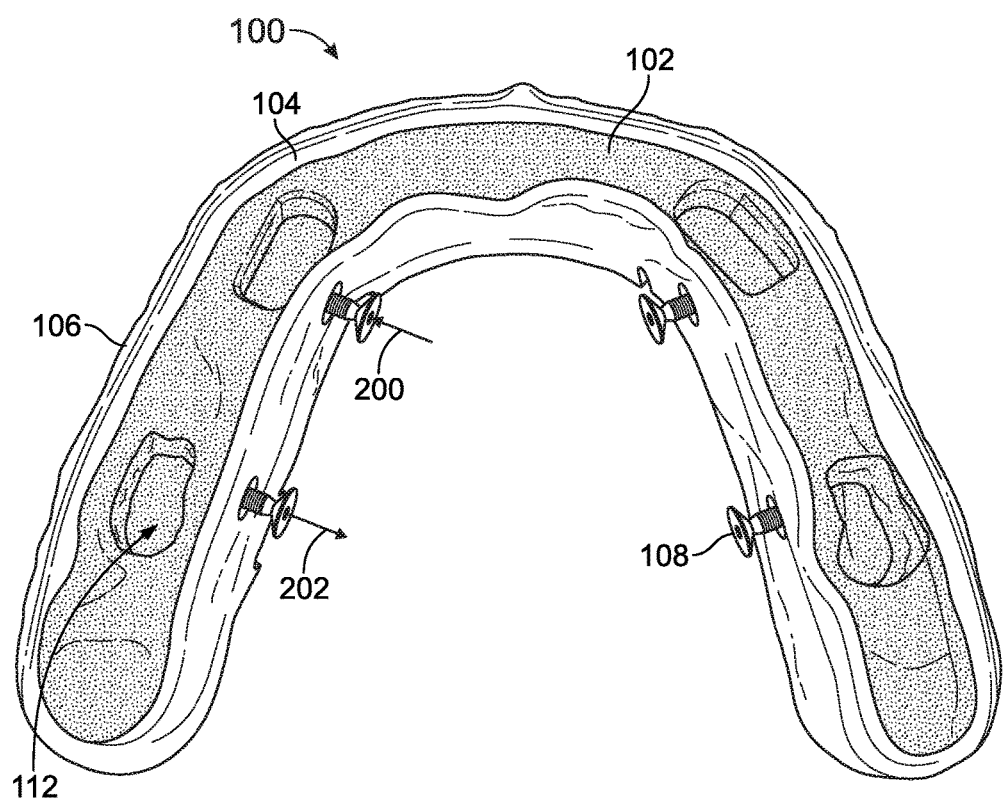
FIG. 2 illustrates another view of the dental prosthetic assembly shown in FIG. 1 according to one embodiment.
Figure 3:
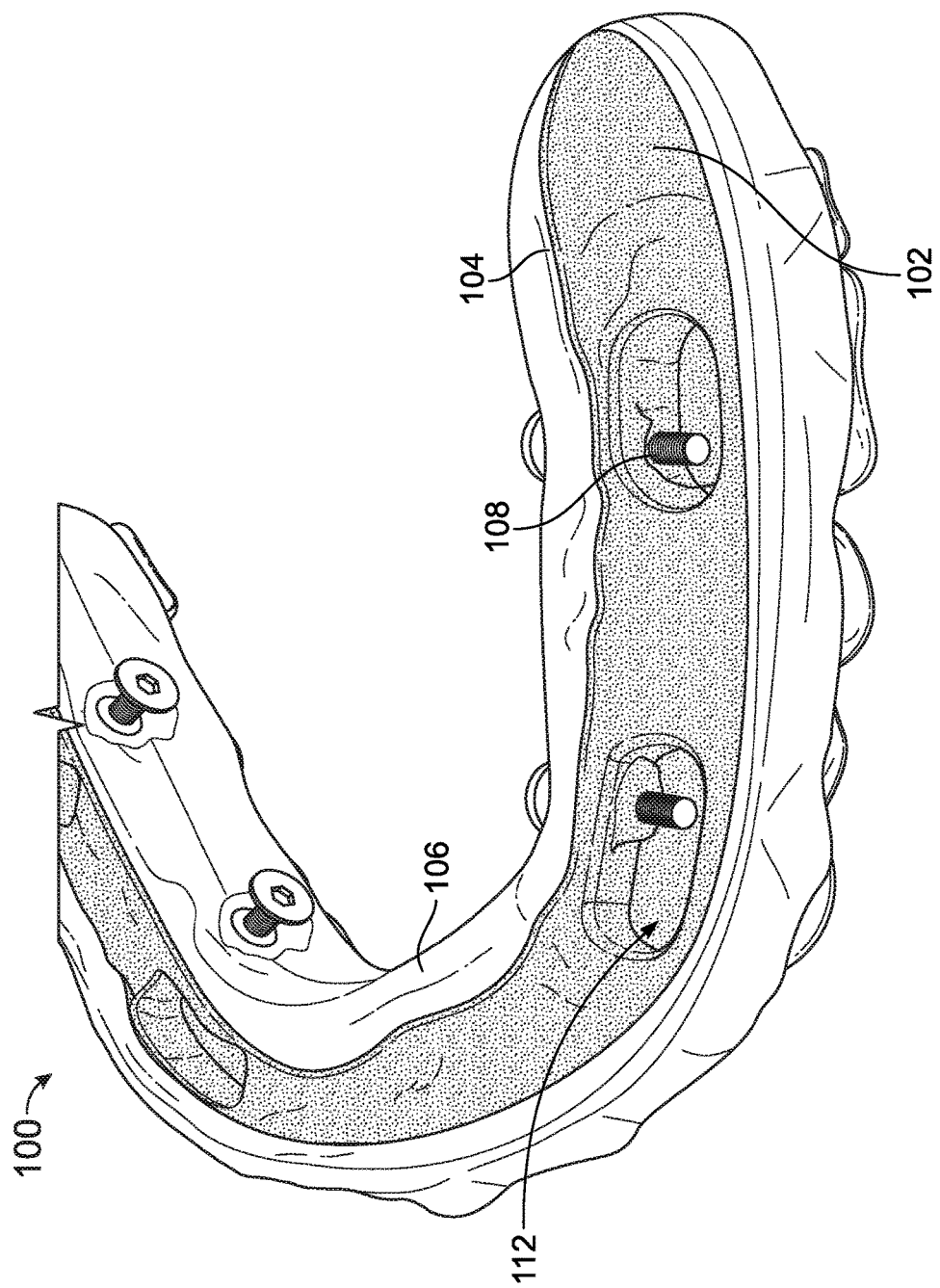
FIG. 3 illustrates another view of the dental prosthetic assembly shown in FIG. 1 according to one embodiment.
Figure 4:
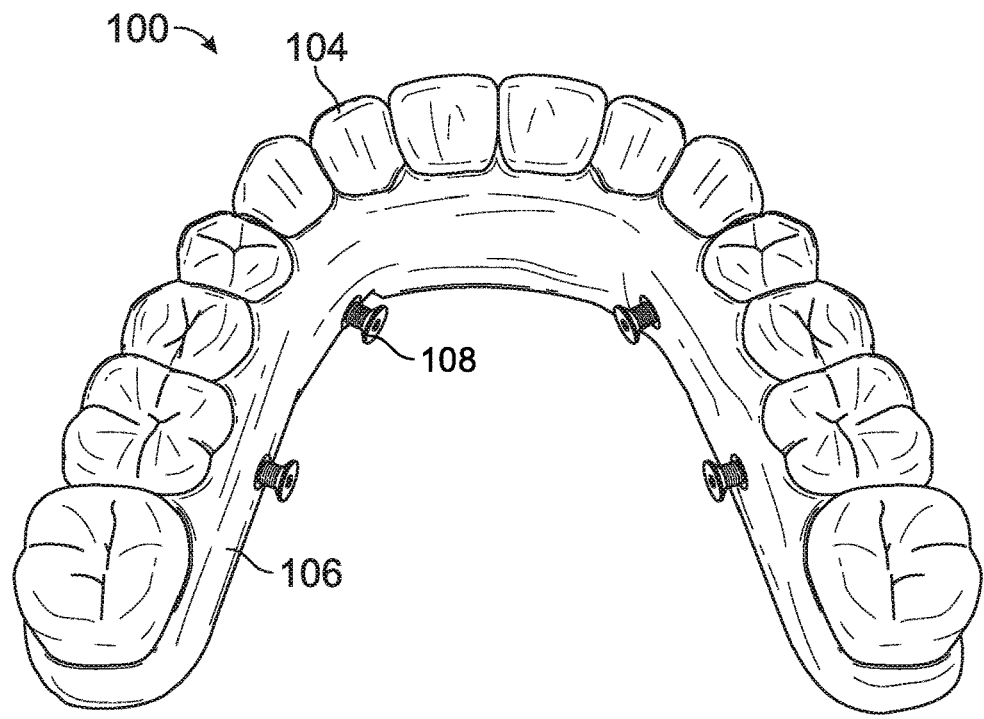
FIG. 4 illustrates another view of the dental prosthetic assembly shown in FIG. 1 according to one embodiment.
Figure 5:
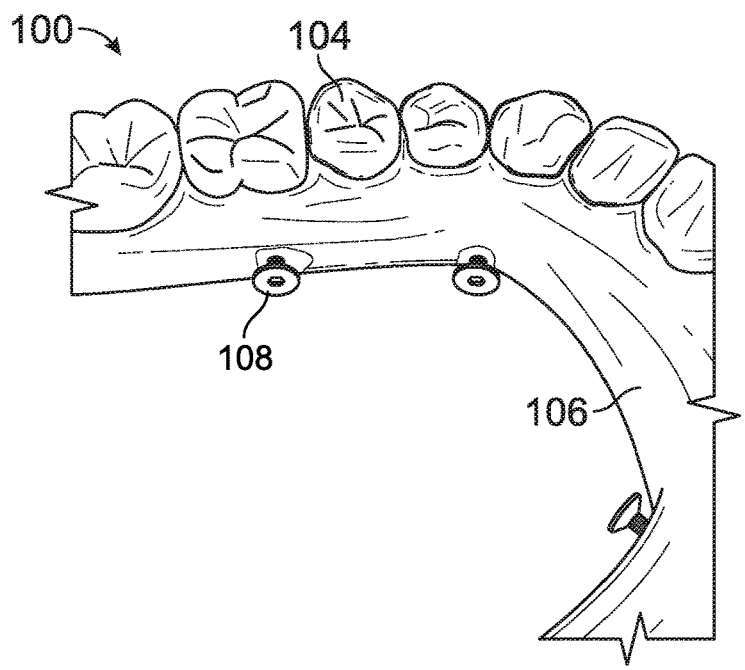
FIG. 5 illustrates another view of the dental prosthetic assembly shown in FIG. 1 according to one embodiment.

FIGS. 1 through 3 illustrate views of a top side of a dental prosthetic assembly 100 according to one embodiment of the inventive subject matter described herein. FIGS. 4 through 7 illustrate views of a bottom side of the dental prosthetic assembly 100 shown in FIGS. 1 through 3. The dental prosthetic assembly 100 includes a reinforcement bar 102 with a polymer and glass-based outer layer 104 on the reinforcement bar 102.

The reinforcement bar 102 is formed from a lightweight material having significant strength. The reinforcement bar 102 may be lighter than other materials currently used in dental prosthetics (e.g., dentures). For example, the reinforcement bar 102 may be lighter than (e.g., have a lower density than) titanium or solid zirconia. The lighter weight of the reinforcement bar 102 can reduce the energy expended for chewing or speaking, thereby reducing the fatigue experienced by persons wearing the dental prosthetic assembly 100 (relative to persons wearing other dentures, such as dentures formed from solid zirconia).

In one embodiment, the reinforcement bar 102 is formed from a copolyester resin material having nanoceramic particles dispersed throughout the bar 102. The reinforcement bar 102 may be semi-flexible to absorb at least some of the mechanical shock that occurs during use of the dental prosthetic assembly 100 (e.g., during chewing). For example, the reinforcement bar 102 may be sufficiently strong to avoid significantly deformation (e.g., when a patient is chewing), but may be at least partially flexible such that the bar 102 can be partially compressed, move, or otherwise change shape by a greater amount relative to a less flexible material, such as titanium, when the reinforcement bar 102 and the less flexible material are subjected to an equivalent force. This can allow for the reinforcement bar 102 to absorb more mechanical shock caused by chewing or talking relative to other materials, such as titanium.

The reinforcement bar 102 may be more flexible than the outer layer 104. For example, when subjected to the same amount of force (e.g., a common magnitude of force, such as 250 pounds per square inch), the reinforcement bar 102 may change shape or absorb more force than the outer layer 104 and other materials, such as titanium and zirconia.

The outer layer 104 on the reinforcement bar 102 can be formed from a mixture of polymer and glass. The polymer in the outer layer 104 can be a highly-filled resin material. The glass in the outer layer 104 can be silanated glass, or another type of glass. The outer layer 104 can be formed by mixing the polymer and glass in liquid form, and pressing the polymer and glass at elevated temperatures and while under vacuum. This can press the material of the outer layer 104 into a highly dense body having little to no porosity. Reducing or eliminating the porosity of the outer layer 104 can assist in reducing bacterial growth in the dental prosthetic assembly 100, which can occur in the more porous materials used in some known dentures (e.g., acrylic). For example, the volume of pores or openings inside the outer layer 104 may be less (e.g., per unit volume) than the volume of pores or openings inside acrylic materials.

The outer layer 104 and the reinforcement bar 102 are chemically bonded to each other to increase the strength of the interface between the outer layer 104 and the reinforcement bar 102 relative to other materials (e.g., titanium and acrylic). In one embodiment, the outer layer 104 and the reinforcement bar 102 are bonded together using a dual cure resin. This resin chemically lutes the outer layer 104 to the reinforcement bar 102 such that the outer layer 104 is held onto the reinforcement bar 102 by the attraction of atoms in the outer layer 104 to atoms in the reinforcement bar 102 through sharing and/or exchanging electrons. The dual cure resin can be cured by exposing the resin to light for a limited period of time to initiate curing. The exposure of the resin to light can be terminated or otherwise end, and the resin can continue to cure on its own and without exposure to the curing light.

In one embodiment, the resin chemically bonds the outer layer 104 to the reinforcement bar 102 using covalent bonds between atoms of the outer layer 104 and the reinforcement bar 102. In contrast, some known dental prosthetics combine materials that are coupled by mechanical bonding, such as a connection formed by interlocked molecules of the materials without any chemical (e.g., covalent) bonds. The stronger chemical bonds between the outer layer 104 and the reinforcement bar 102 can reduce the likelihood of or prevent the separation of the outer layer 104 from the reinforcement bar 102. This type of separation can occur with other combinations of materials that do not coupled by chemical bonds, such as titanium and acrylic.

An exterior coating 106 is provided on the outer layer 104 to provide a natural look to the dental prosthetic assembly 100. This exterior coating 106 can be formed from a flowable composite polymer material having a coloring to appear like tissue inside a mouth. As shown in FIGS. 4 through 7, the exterior coating 106 may not cover all of the bottom side (e.g., the teeth side) of the dental prosthetic assembly 100. The outer layer 104 may be formed into the shape of teeth, such as by milling part of the material used to form the outer layer 104.

The dental prosthetic assembly 100 also includes a coupling system that secures the dental prosthetic assembly 100 to the mouth of a patient. Part of the coupling system is connected with the reinforcement bar 102 and outer layer 104, while the remaining part of the coupling system is connected with the mouth of the patient. FIGS. 1 through 7 illustrate the part of the coupling system connected with the reinforcement bar 102 and the outer layer 104. This part of the coupling system includes plural elongated pins 108 that extend into lateral openings 110 (shown in FIG. 1) through the exterior coating 106 and the outer layer 104 into the reinforcement bar 102. The lateral openings 110 are oriented along directions that is transverse to the direction in which the teeth formed by the outer layer 104 in the assembly 100 extend. For example, if the artificial teeth in the assembly 100 extend along vertical directions, then the lateral openings 110 are oriented along horizontal directions that are perpendicular to the vertical directions.

The reinforcement bar 102 includes several interior receptacles 112. The receptacles 112 are voids inside the reinforcement bar 102. The receptacles 112 accessible to the pins 108 through the lateral openings 110. For example, the pins 108 may move toward and partially into the receptacles 112 through corresponding lateral openings 110 along lateral insertion directions 200 (shown in FIG. 2). The elongated pins 108 may move away from and partially out of the receptacles 112 through the corresponding lateral openings 110 along opposite lateral removal directions 202 (shown in FIG. 2). Each of the pins 108 may be moved along a corresponding insertion direction 200 in order to secure (e.g., lock) the dental prosthetic assembly 100 into a mouth and may be moved along a corresponding removal direction 202 in order to detach (e.g., unlock) the dental prosthetic assembly 100 from the mouth. FIGS. 1, 2, 4, and 5 show the pins 108 in unlocked or detached positions (also referred to as an unlocked or detached state), where the pins 108 have been at least partially moved out of the receptacles 112. The top most two pins 108 in FIG. 3 and the left most two pins 108 in FIG. 6 also are in the unlocked or detached positions. As described below, this disengages the pins 108 from complementary or matching holes in implant abutments or anchors affixed to the inside of a patient's mouth.

Figure 6:
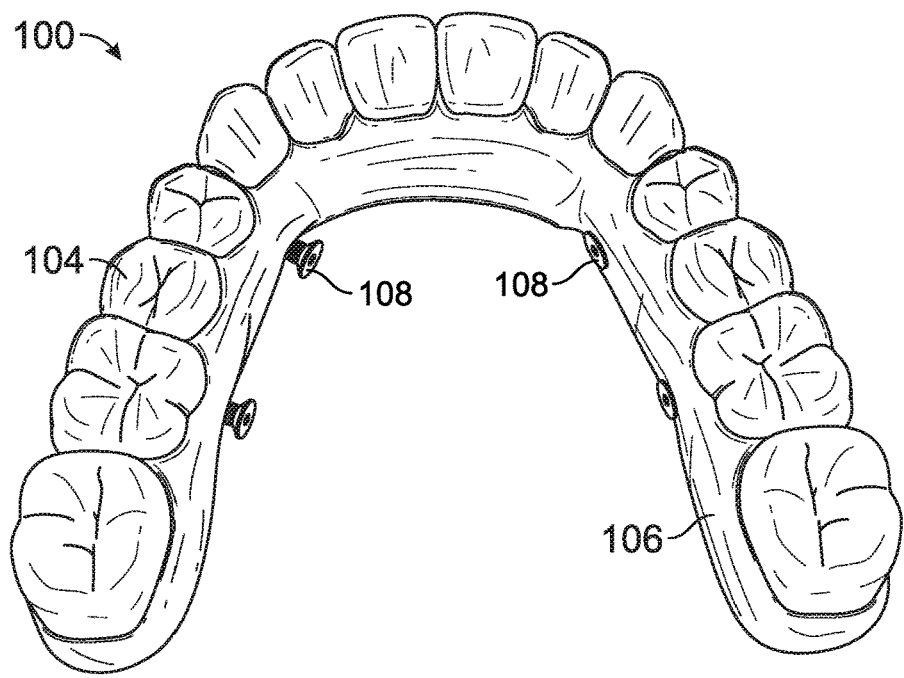
FIG. 6 illustrates another view of the dental prosthetic assembly shown in FIG. 1 according to one embodiment.
Figure 7:
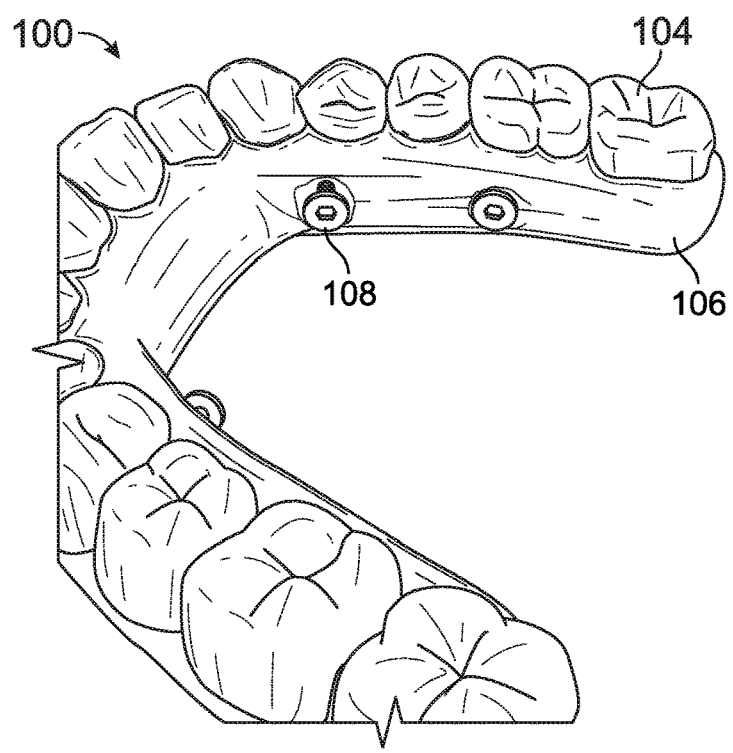
FIG. 7 illustrates another view of the dental prosthetic assembly shown in FIG. 1 according to one embodiment.

The bottom most two pins 108 in FIG. 3, the right most two pins 108 in FIG. 6, and the pins 108 in FIG. 7 are in locked or secured positions (also referred to as a locked or secured state), where the pins 108 have been at least partially moved into the receptacles 112. As described below, this engages the pins 108 into complementary or matching holes in implant anchors affixed to the inside of a patient's mouth to lock or secure the dental prosthetic assembly 100 in the mouth.

Figure 8:
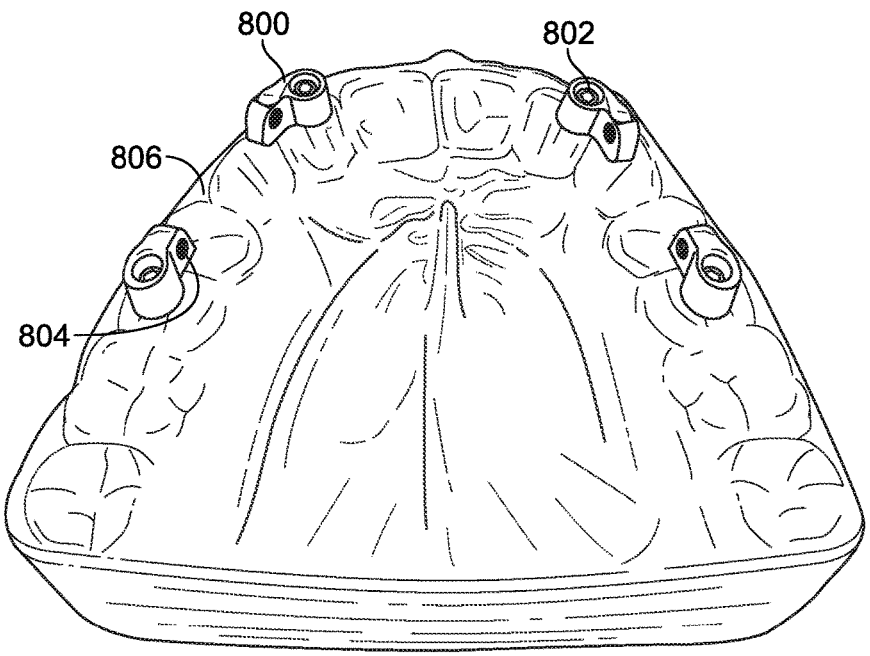
FIG. 8 illustrates implant abutments of a coupling system according to one embodiment.
Figure 9:
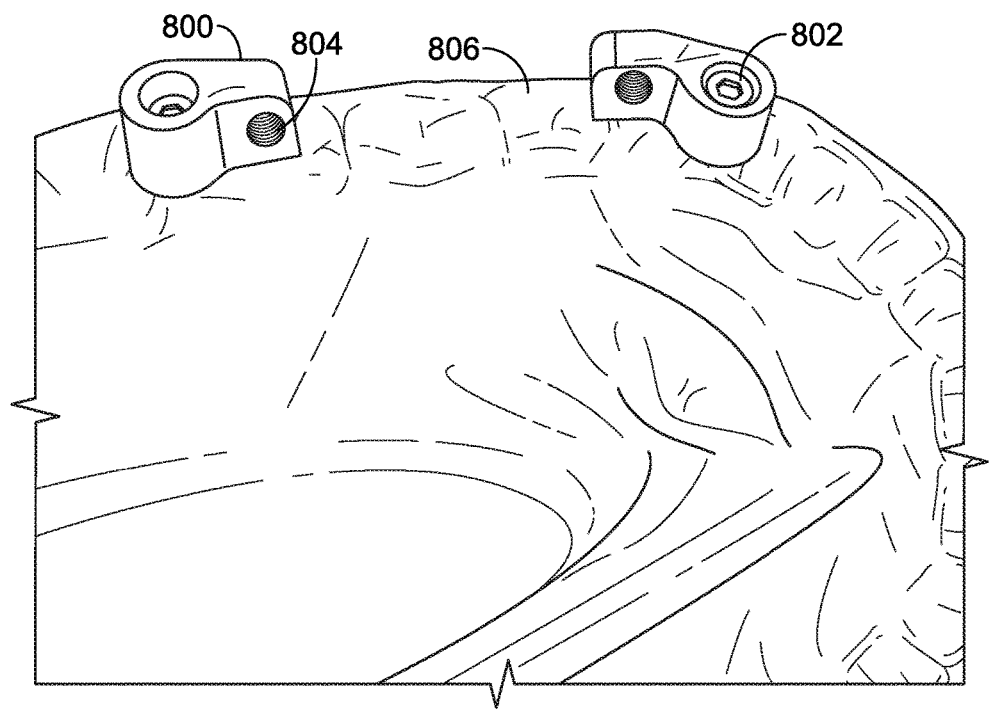
FIG. 9 illustrates implant abutments of the coupling system according to one embodiment.

FIGS. 8 and 9 illustrate implant anchors 800 of the coupling system according to one embodiment. The implant anchors 800 are secured to bone beneath a tissue surface 806 of the inside of a patient's mouth. This bone may be the maxilla (with the tissue surface 806 being the roof of the mouth) or the mandible (with the tissue surface 806 being the opposite side of the mouth).

The implant anchors 800 may be secured to the mouth using fasteners 802, such as screws. The implant anchors 800 include holes 804 shaped and sized to receive the pins 108 (shown in FIGS. 1 through 7) when the pins 108 are in the locked or secured position or state. For example, the dental prosthetic assembly 100 (shown in FIGS. 1 through 7) can be placed into a patient's mouth with the pins 108 retracted into the unlocked position.

The implant anchors 800 may be received into the recesses 112 (shown in FIGS. 1 through 3) of the reinforcement bar 102 (shown in FIGS. 1 through 7). The pins 108 may then be actuated (e.g., laterally moved relative to the direction in which the teeth extend in the mouth) in the insertion directions 200 (shown in FIG. 2). This moves the pins 108 into or through the holes 804 in the implant anchors 800. With the pins 108 extending into or through these holes 804, the dental prosthetic assembly 100 is secured to the patient's mount. For example, when the assembly 100 is coupled to the top side of a patient's mouth, the assembly 100 is prevented from being moved downward away from the roof of the patient's mouth by the pins 108 extending through the holes 804 in the anchors 800. The assembly 100 may similarly be coupled to the bottom a patient's mouth using additional anchors 800 fixed to the patient's mouth on the bottom of the inside of the patient's mouth. To remove the dental prosthetic assembly 100 from the patient's mouth, the pins 108 are moved in the opposite retraction direction 202 (shown in FIG. 2). This moves the pins 108 out of the holes 108 in the implant anchors 800 so that the dental prosthetic assembly 100 can be removed from the patient's mouth.

Figure 10:
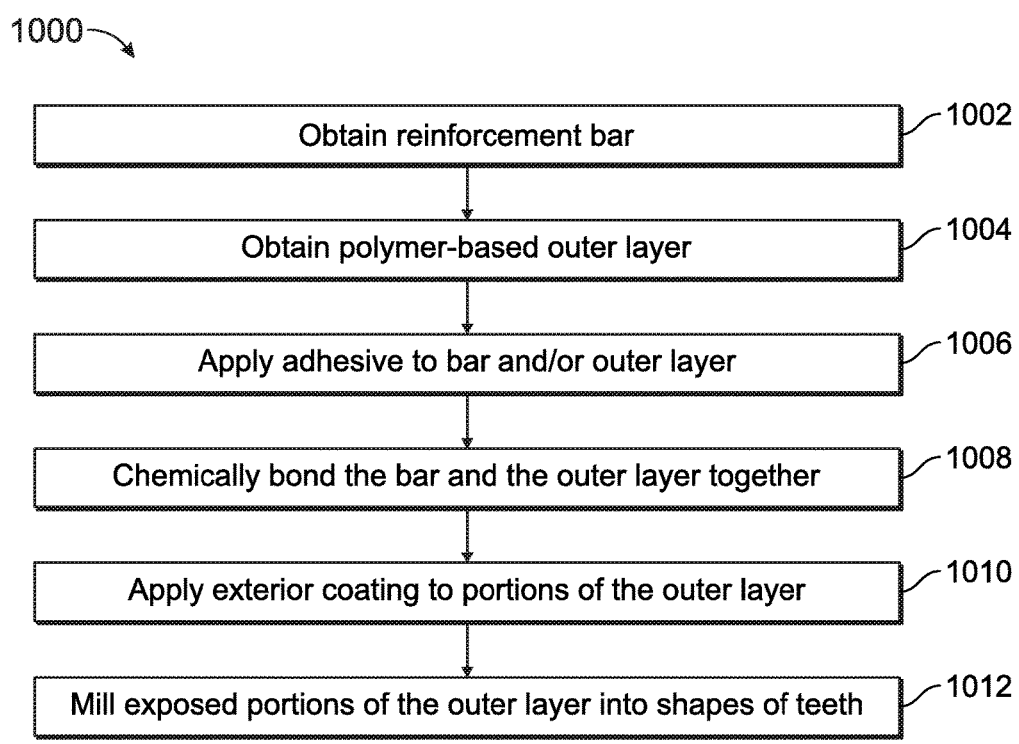
FIG. 10 illustrates a flowchart of one embodiment of a method for providing a dental prosthetic assembly.

FIG. 10 illustrates a flowchart of one embodiment of a method 1000 for providing a dental prosthetic assembly. The method 1000 may be used to manufacture the dental prosthetic assembly 100 shown in FIGS. 1 through 7. At 1002, a reinforcement bar is obtained. The reinforcement bar may be molded using a lightweight material having significant strength, such as a copolyester resin material having nanoceramic particles dispersed throughout. At 1004, a polymer-based outer layer is obtained. This layer may be a body formed from a mixture of polymer and glass, such as a mixture of a highly filled resin material and silanated glass. The polymer-based outer layer may be molded into a shape that fits around the reinforcement bar. Part of the polymer-based outer layer may protrude outward so that this part can be milled into the shape of teeth of the dental prosthetic assembly.

At 1006, an adhesive is applied to the reinforcement bar and/or polymer-based outer layer. For example, a dual cure resin may be applied to the surface of the reinforcement bar that will face and/or engage the polymer-based outer layer, and/or the resin may be applied to the surface of the polymer-based outer layer that will face and/or engage the reinforcement bar. At 1008, the reinforcement bar and the polymer-based outer layer are chemically bonded together. The adhesive can cure to chemically bond the reinforcement bar and the polymer-based outer layer together. This prevents the polymer-based outer layer from separating from the reinforcement bar after continued use of the dental prosthetic assembly.

At 1010, an exterior coating is applied to portions of the polymer-based outer layer. This coating provides a natural look to the dental prosthetic assembly, such as by having a color of tissue (e.g., a pink color). This exterior coating can be formed from a flowable composite polymer material having a coloring to appear like tissue inside a mouth. The coating may not be applied over the portions of the polymer-based outer layer that will form the teeth of the dental prosthetic assembly. At 1012, the exposed portions of the polymer-based outer layer are milled into the shapes of teeth. For example, the portions of the polymer-based outer layer that were not covered by the exterior coating may be milled into the shape of teeth to complete assembly of the dental prosthetic assembly.

In one embodiment, a dental prosthetic assembly includes a flexible reinforcement bar and a polymer-based outer layer chemically bonded to the reinforcement bar outside of the reinforcement bar. The reinforcement bar forms an interior of the dental prosthetic assembly and at least a portion of the outer layer forms teeth of the dental prosthetic assembly.

The flexible reinforcement bar can have a density that is less than density of titanium or density of zirconia. The flexible reinforcement bar is more flexible than titanium when subjected to a common amount of force in one example. Optionally, the flexible reinforcement bar is formed from a copolyester resin having nanoceramic particles in the resin. The flexible reinforcement bar can be more flexible than the polymer-based outer layer when subjected to a common amount of force.

In one example, the polymer-based outer layer is formed from a glass filled resin. Optionally, the polymer-based outer layer is formed from a resin having silanted glass in the resin. The polymer-based outer layer can be less porous than acrylic.

The assembly can also include a dual cure resin chemically bonding the reinforcement bar to the polymer-based outer layer. The assembly optionally can include a tissue-colored exterior coating on less than an entirety of an exterior surface of the polymer-based outer layer.

In one embodiment, a coupling system of a dental prosthetic assembly includes pins disposed in openings extending into the dental prosthetic assembly and implant anchors configured to be coupled with a mouth of a patient. The implant anchors have holes configured to receive the pins. The pins secure the dental prosthetic assembly to the implant anchors by moving into the dental prosthetic assembly through the openings and into the holes of the implant anchors.

The openings in the dental prosthetic assembly can be laterally oriented with respect to teeth of the dental prosthetic assembly, and the pins are actuated in first lateral directions in the openings to secure the dental prosthetic assembly to the implant anchors. The pins can be actuated in opposite second lateral directions in the openings to detach the dental prosthetic assembly from the implant anchors.

Optionally, the implant anchors are sized to fit into recesses in the dental prosthetic assembly. The openings in the dental prosthetic assembly can laterally extend from outside of the dental prosthetic assembly into the recesses in the dental prosthetic assembly.

In one embodiment, a method includes obtaining a flexible reinforcement bar, obtaining a polymer-based outer layer, chemically bonding the reinforcement bar with the polymer-based outer layer, and milling artificial teeth into the polymer-based outer layer to form a dental prosthetic assembly. The reinforcement bar forms an interior of the dental prosthetic assembly.

In one example, the flexible reinforcement bar has a density that is less than density of titanium or density of zirconia. The flexible reinforcement bar can be more flexible than titanium when subjected to a common amount of force. The flexible reinforcement bar can be formed from a copolyester resin having nanoceramic particles in the resin. Optionally, the flexible reinforcement bar is more flexible than the polymer-based outer layer when subjected to a common amount of force.

The polymer-based outer layer can be formed from a glass filled resin. In one example, the polymer-based outer layer is formed from a resin having silanted glass in the resin. The polymer-based outer layer can be less porous than acrylic.

Chemically bonding the reinforcement bar with the outer layer can include applying a dual cure resin to one or more of the reinforcement bar or the outer layer. The method may optionally also include applying a tissue-colored exterior coating on less than an entirety of an exterior surface of the polymer-based outer layer.

The above description is illustrative and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are example embodiments. Other embodiments may be apparent to one of ordinary skill in the art upon reviewing the above description. The scope of the inventive subject matter should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure. And, as used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A dental prosthetic assembly comprising:
a semi-flexible reinforcement bar; and
a polymer and glass outer layer chemically luted to the semi-flexible reinforcement bar outside of the reinforcement bar using a dual cure bonding system, wherein the reinforcement bar forms an interior of the dental prosthetic assembly and at least a portion of the polymer and glass outer layer forms teeth of the dental prosthetic assembly.

2. The dental prosthetic assembly of claim 1, wherein the semi-flexible reinforcement bar has a density that is less than density of titanium or density of zirconia.

3. The dental prosthetic assembly of claim 1, wherein the semi-flexible reinforcement bar is more flexible than titanium when the semi-flexible reinforcement bar and the titanium are subjected to a common amount of force.

4. The dental prosthetic assembly of claim 1, wherein the semi-flexible reinforcement bar is formed from a copolyester resin having nanoceramic particles in the resin.

5. The dental prosthetic assembly of claim 1, wherein the semi-flexible reinforcement bar is more flexible than the polymer and glass outer layer when the semi-flexible reinforcement bar and the polymer and glass outer layer are subjected to a common amount of force.

6. The dental prosthetic assembly of claim 1, wherein the polymer and glass outer layer is formed from a glass filled resin.

7. The dental prosthetic assembly of claim 1, wherein the polymer and glass outer layer is formed from a resin having silanted glass in the resin.

8. The dental prosthetic assembly of claim 1, wherein the polymer and glass outer layer is less porous than acrylic.

9. The dental prosthetic assembly of claim 1, further comprising a dual cure resin that chemically bonds the reinforcement bar to the polymer and glass outer layer.

10. The dental prosthetic assembly of claim 1, further comprising a tissue-colored exterior coating on less than an entirety of an exterior surface of the polymer and glass outer layer.

* * * * *